United States Patent [19]

Freed et al.

[11] Patent Number: 4,562,255
[45] Date of Patent: Dec. 31, 1985

[54] SUBSTITUTED BI-ALICYCLIC IMIDES

[75] Inventors: Meier E. Freed, Paoli, Pa.; Magid A. Abou-Gharbia, Wilmington, Del.

[73] Assignee: American Home Products Corporation, New York, N.Y.

[21] Appl. No.: 595,138

[22] Filed: Mar. 30, 1984

[51] Int. Cl.[4] .................. C07D 403/14; C07D 405/14; C07D 409/14
[52] U.S. Cl. ................................. 544/357; 260/243.3; 260/244.4; 260/245.5; 260/245.7; 544/295; 544/331; 544/364; 544/366; 544/373; 544/405; 546/269; 546/270; 546/273; 548/251; 548/253; 548/336
[58] Field of Search ............... 544/295, 357, 364, 366, 544/373, 331, 405; 548/253, 336, 251; 546/269, 270, 273; 260/243.3, 245.5

[56] References Cited

U.S. PATENT DOCUMENTS 3,717,634  2/1973  Wu et al. ........................ 424/251
4,355,031 10/1982  Demerson et al. ............... 544/295

FOREIGN PATENT DOCUMENTS 893378 12/1982 Belgium .

OTHER PUBLICATIONS

Korgaonkar et al., "Chemical Abstracts", vol. 101, 1984, col. 101:23432k.

Primary Examiner—Glennon H. Hollrah
Assistant Examiner—James H. Turnipseed
Attorney, Agent, or Firm—George Tarnowski

[57] ABSTRACT

There are disclosed compounds having the formula

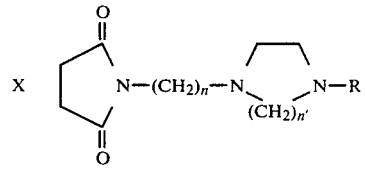

wherein X is a group selected from

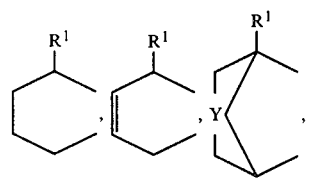

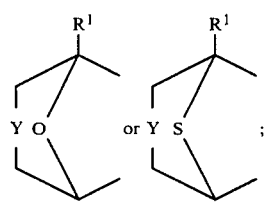

Y represents a single or double bond;
$R^1$ is hydrogen or lower alkyl;
n is an integer 2–4;
n' is an integer 1–2; and
R is 2-pyrimidinyl, 2-pyridinyl, 2-pyrazinyl, halo-substituted 2-pyrazinyl, 5-tetrazolyl, phenyl or phenyl substituted by halo, lower alkyl or lower alkoxy;

and the pharmacologically acceptable salts thereof, which exhibit anti-hypertensive activity.

4 Claims, No Drawings

SUBSTITUTED BI-ALICYCLIC IMIDES

DESCRIPTION OF THE INVENTION

This invention relates to novel compounds having antihypertensive activity and being characterized by the general formula:

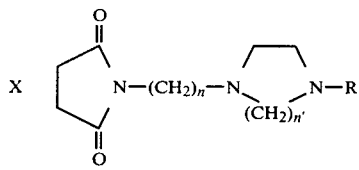

wherein X is a group selected from

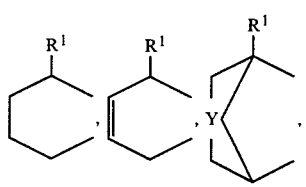

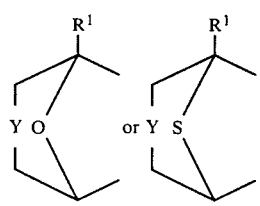

Y represents a single or double bond;
$R^1$ is hydrogen or lower alkyl;
n is an integer 2–4;
n' is an integer 1–2; and
R is 2-pyrimidinyl, 2-pyridinyl, 2-pyrazinyl, halo-substituted 2-pyrazinyl, 5-tetrazolyl, phenyl or phenyl substituted by halo, lower alkyl or lower alkoxy; and the pharmacologically acceptable salts thereof.

The term "lower alkyl" refers to moieties having 1–6 carbon atoms in the carbon chain. The term "halo" refers to fluoro, chloro and bromo.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of the invention may be prepared by a variety of synthetic routes using conventional methods. For example, an appropriately substituted 3,6-endoxyhexahydrophthalic acid anhydride can be reacted with 1-(4-aminoloweralkyl)-4-(2-pyrimidinyl)piperazine under prolonged heating:

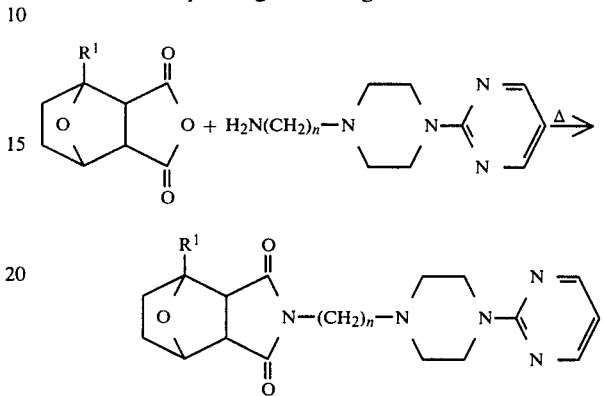

wherein $R^1$ and n are as defined hereinbefore. In an alterate preparative route, an appropriately substituted 3,6-endoxyhexahydrophthalimide can be reacted with a suitable dihalo loweralkane, to yield an intermediate product which can then be reacted with 4-(2-pyrimidinyl)piperazine to yield the same final product as obtained in the first preparative route discussed, supra.

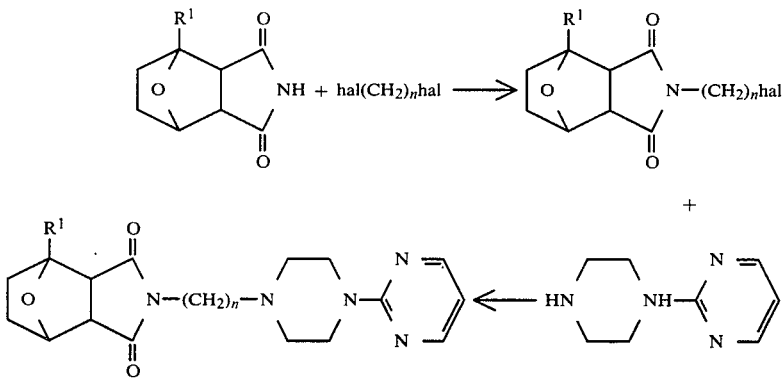

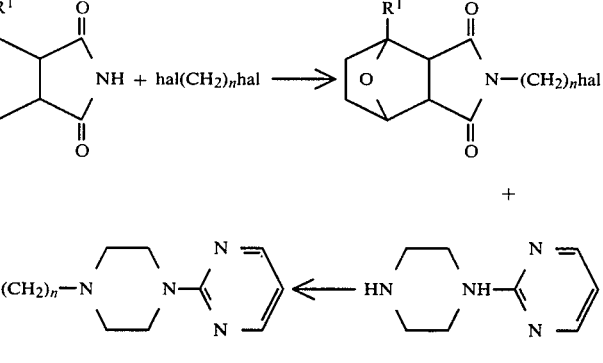

Of course, other methods of preparation, which will occur to those skilled in the art, may also be employed to prepare the compounds of the invention.

The starting materials used in the above-described preparative routes are commercially available, or can be made according to procedures taught in the chemical literature.

The compounds of the invention may exist either in the form of the free base or the pharmacologically acceptable salts. Methods for converting one such form to another will be obvious to one skilled in the chemical arts.

The compounds of the invention are effective in lowering blood pressures as shown in standard tests using hypertensive rats. Such tests are conducted on spontaneously hypertensive rats, with test groups and control groups consisting of 4 rats, and the test compounds and reference compounds being administered orally. Systolic blood pressures are measured by indirect tail plethysmography (using a Narco Bio-Systems system) with rats being warmed to 38° C. for 10 minutes prior to measurement to increase the accuracy of the readings. Readings are taken prior to drug administration and periodically thereafter at 1.5, 4, and 24 hours after administration. Systolic pressure and heart rate data are collected in an Hewlett Packard 88 computer. Data are grouped and summarized, with the mean change in pressure and heart rate at each time period calculated. Data cards are printed for each compound tested. These cards include compound name, dose tested, individual rat I.D., control systolic pressure and heart rate and change in both parameter for each rat, and the group mean values for each measurement. Reference compounds used include phenolamine and hydralazine.

When administered in doses of 5–50 mg/kg, the compounds of the invention demonstrate a significant ability to reduce blood pressure.

When tested in spontaneously hypertensive rats as described above, compounds of the invention gave the following results:

| Compound of Example No. | Dose (mg/kg) | Systolic Decrease in Blood Pressure (mm Hg) |
| --- | --- | --- |
| 1 | 25 (1.5 hrs) | −27 |
|   | 50 (1.5 hrs) | −70 |
| 2 | 5 (1.5 hrs) | −43 |
|   | 25 (1.5 hrs) | −55 |
|   | 25 (4.0 hrs) | −34 |
|   | 50 (1.5 hrs) | −88 |
|   | 50 (4.0 hrs) | −83 |
| 3 | 10 (1.5 hrs) | −55 |
|   | 50 (1.5 hrs) | −40 |
|   | 50 (4.0 hrs) | −70 |
| 4 | 10 (1.5 hrs) | −37 |
|   | 50 (1.5 hrs) | −67 |
| 5 | 5 (1.5 hrs) | −18 |
|   | 50 (1.5 hrs) | −111 |
|   | 50 (4.0 hrs) | −84 |
| 6 | 10 (4.0 hrs) | −28 |

The reference compounds give the following results in the above-described test procedure:

| Drug | Dose | SBP Change (1.5 hr) |
| --- | --- | --- |
| Phentolamine | 5 mg/kg | −71 mm Hg |
| Hydralazine | 1 mg/kg | −55 mm Hg |

When employed to lower blood pressures, the effective dosage of the substance active for such treatment will vary according to the particular compound being employed, the severity and nature of condition being treated. Therapy should be initiated at lower doses (in mg/kg/day) in the effective ranges given above for the prescribed activity, the dosage thereafter being increased, if necessary, to produce the desired anti-hypertensive effect.

When the compounds of the invention are employed as anti-hypertensive agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compunds may be encapsulated with or without other carriers. In all cases, the proportion of active ingredients in said compositions both solid and liquid will be at least to impart the desired activity thereto on oral administration. The compounds may also be injected parenterally in which case they are used in the form of a sterile solution containing other solutes, for example, enough saline or glucose to make the solution isotonic.

The following examples illustrate the preparation of compounds within the scope of the invention.

EXAMPLE 1

Hexahydro-4-methyl-2-[4-[4-(2-pyrimidinyl)-1-piperazinyl]butyl]-4,7-epoxy-1H-isoindole-1,3(2H)-dione, fumarate A three neck flask is charged with 4 g (0.022 mole) of 3-methyl-3,6-endoxohexahydrophthalic acid anhydride (powdered) and 1-(4-aminobutyl-4-[2-pyrimidinyl]piperazine, 5.2 g (0.02 mole). The reaction is heated at 150° C. for 18 hours, then at 180° C. for an additional 6 hours. After cooling to room temperature the mixture is extracted with boiling 2-propanol, filtered, and the filtrate allowed to cool. 4 g of free base of the title compound are obtained. Recrystallization from 2-propanol pentane yields the free base compound with a melting point of 139°–140° C. The fumaric acid salt is prepared in acetone and has a melting point of 167°–168° C.

Analysis for: $C_{21}H_{29}O_3N_5 \cdot C_4H_4O_4$ Calculated: C, 58.24; H, 6.45; N, 13.99 Found: C, 58.22; H, 6.36; N, 13.32.

EXAMPLE 2

Hexahydro-2-[4-[4-(2-pyrimidinyl)-1-piperazinyl]-butyl]-4,7-epoxy-1H-isoindole-1,3(2H)-dione, hydrochloride A mixture of 1.68 g 3,6-endoxo-hexahydrophthalic anhydride (0.01 m) and 2.35 g of 1-(4-aminobutyl)-4-(2-pyrimidinyl)piperazine (0.01 m) is warmed to 120° C. Liquefaction occurs. Stirring and heating at 140° C. are continued for 16 hours, then at 200° C. for 2 hours. After cooling, the solid is crystallized from methylene dichloridehexane to yield the free base compound with a melting point of 136°–137° C. The hydrochloride salt is prepared in 2-propanol and has a melting of 156°–157° C.

Analysis for: $C_{20}H_{27}N_5O_3 \cdot HCl$ Calculated: C, 56.93; H, 6.69; N, 16.60; Cl, 8.40 Found: C, 56.76; H, 6.87; N, 15.90; Cl, 8.39.

EXAMPLE 3

Hexahydro-2-[4-[4(2-pyrimidinyl)-1-piperazinyl]butyl]-1H-isoindole-1,3(2H)-dione, fumarate Cis-1,2-cyclohexane dicarboxylic acid anhydride (6g, 0.04 m) and 1-(4-aminobutyl)-4-[2-pyrimidinyl]piperazine (10 g, 0.042 m) are mixed. (Note: the reaction is exothermic, requiring cooling.) After the initial exothermic reaction ceases, the reaction mixture is heated at 170° C. for 2 hours. After cooling the reaction mixture the product is crystallized from ether-pentane and has a melting point of 95°–97° C. Yield: 11.8 g. The fumaric acid salt is prepared in acetone and has a melting point of 181°–183° C.

Analysis for: $C_{20}H_{29}N_5O_2 \cdot C_4H_4O_4$ Calculated: C, 59.12; H, 6.82; N, 14.36 Found: C, 58.73; H, 6.65; N, 14.34.

EXAMPLE 4

3a,4,7,7a-Tetrahydro-2-[4-[4-(2-pyrimidinyl)-1-piperazinyl]butyl]-4,7-methano-1H-isoindole-1,3(2H)-dione, fumarate (1:1) hemihydrate A mixture of 5-norbornene-endo-2,3-dicarboxylic acid anhydride (1.96 g, 0.01 mole) and 1-(4-aminobutyl)-4-(2-pyrimidinyl)piperazine (3.0 g, 0.013 mole) is heated on an oil bath at 100° C. for 1 hour. The temperature is raised to 150° C. and stirring is continued at the temperature for two hours. The reaction mixture is cooled and triturated with a petroleum ether-ethanol (2:1) mixture, with cooling. The separated solid is filtered and recrystallized from ether to give colorless needles having a melting point of 39°–40° C., which is converted to the fumarate hemihydrate in ethanol which has a melting point of 192°–194° C.

Analysis for: $C_{21}H_{27}N_5O_2 \cdot C_4H_4O_4 \cdot \frac{1}{2}H_2O$ Calculated: C, 59.47; H, 6.38; N, 13.98 Found: C, 59.28; H, 6.32; N, 13.98.

EXAMPLE 5

Hexahydro-2-[4-[4-[2-pyrimidinyl]-1-piperazinyl]-butyl]-4,7-methano-1H-isoindole-1,3(2H)-dione, fumarate (1:1) hemihydrate A mixture of norbornane-endo-2,3-dicarboxylic acid anhydride (2.3 g, 0.013 mole) and 1-(4-aminobutyl)-4-(2-pyrimidinyl)piperazine (3.5 g, 0.014 mole) is heated on an oil bath at 120° C. for ½ hour with stirring under nitrogen. The temperature is raised to 160°–170° C. and heating is continued for two hours. The reaction mixture is cooled and is triturated with alcohol and the separated solid (m.p. 46°–50° C.) is converted to the fumarate hemihydrate salt in ethanol which has a melting point of 166°–168° C.

Analysis for: $C_{21}H_{29}N_5O_2 \cdot C_4H_4O_4 \cdot \frac{1}{2}H_2O$ Calculated: C, 59.05; H, 6.69; N, 13.77 Found: C, 59.14; H, 6.68; N, 13.68.

EXAMPLE 6

Hexahydro-2-[4-[4-[2-chloropyrazinyl]-1-piperazinyl]-butyl]-4,7-epoxy-1H-isoindole-1,3(2H)-dione, dihydrochloride, ⅓ ethanolate Following the procedure of Example 1 and using 3,6-endoxyhexahydrophthalic anhydride and 1-(4-aminobutyl)-4-[2-(6-chloropyrazinyl)]piperazine, as starting materials, there is obtained the title compound after converting the free base compound to the hydrochloride salt. The title compound has a melting point of 255°–256° C.

Analysis for: $C_{20}H_{26}ClN_5O_3 \cdot 2\ HCl \cdot \frac{1}{3}C_2H_6O$ Calculated: C, 48.84; H, 5.95; N, 13.70 Found: C, 48.57; H, 5.89; N, 13.38.

EXAMPLE 7

Following the procedure of Example 1 and using the indicated starting materials, there are obtained the indicated final products:

| | Starting Materials | Final Products |
|---|---|---|
| (a) | 3,6-endoxohexahydrophthalic anhydride/1-(4-aminobutyl)-4-(2-pyrazinyl)piperazine | Hexahydro-2-[4-[4-(2-pyrazinyl)-1-piperazinyl]butyl]-4,7-epoxy-1H—isoindole-1,3(2H)—dione |
| (b) | 3,6-endoxohexahydrophthalic anhydride/1-(2-aminoethyl)-4-(2-pyrimidinyl)piperazine | Hexahydro-2-[2-[4-(2-pyrimidinyl)-1-piperazinyl]ethyl]-4,7-epoxy-1H—isoindole-1,3(2H)—dione |
| (c) | 3,6-endoxohexahydrophthalic anhydride/1-(4-aminobutyl)-4-(5-tetrazolyl)piperazine | Hexahydro-2-[4-[4-(5-tetrazolyl)-1-piperazinyl]butyl]-4,7-epoxy-1H—isoindole-1,3(2H)—dione |

What is claimed is:

1. A compound having the formula

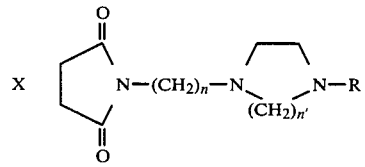

wherein X is a group selected from

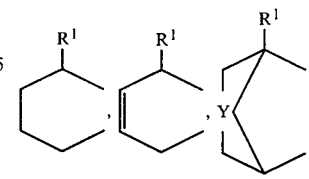

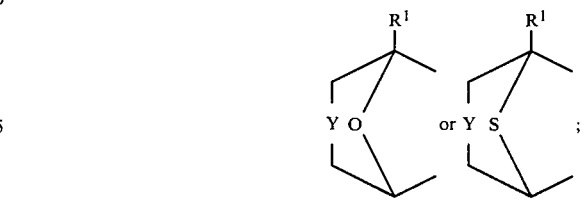

Y represents a single or double bond;
$R^1$ is hydrogen or lower alkyl;
n is an integer 2–4;
n' is an integer 1–2; and
R is [2-pyrimidinyl, 2-pyridinyl,] 2-pyrazinyl, halo-substituted 2-pyrazinyl or 5-tetrazolyl;
and the pharmacologically acceptable salts thereof.

2. A compound of claim 1, having the name hexahydro-2-[4-[4-[2-chloropyrazinyl]-1-piperazinyl]butyl]-4,7-epoxy-1H-isoindole-1,3 (2H)-dione.

3. A compound of claim 1, having the name hexahydro-2-[4-[4-(2-pyrazinyl)-1-piperazinyl]butyl]-4,7-epoxy-1H-isoindole-1,3(2H)-dione.

4. A compound of claim 1 having the name hexahydro-2-[4-[4-(5-tetrazoyl)-1-piperazinyl]butyl]-4,7-epoxy-1H-isoindole-1,3(2H)-dione.

* * * * *

UNITED STATES PATENT AND TRADEMARK OFFICE
CERTIFICATE OF CORRECTION

PATENT NO. : 4,562,255
DATED : Dec. 31, 1985
INVENTOR(S) : Freed et al

It is certified that error appears in the above-identified patent and that said Letters Patent is hereby corrected as shown below:

IN THE CLAIMS:

Please amend claim 1 as follows:

Claim 1

Line 3 from the bottom, delete "[2-pyrimidinyl, 2-pyridinyl,]".

Signed and Sealed this

Sixteenth Day of February, 1988

Attest:

DONALD J. QUIGG

Attesting Officer

Commissioner of Patents and Trademarks